United States Patent [19]

Gunasekera et al.

[11] Patent Number: 4,939,168

[45] Date of Patent: Jul. 3, 1990

[54] DISCODERMOLIDE COMPOUNDS, COMPOSITIONS CONTAINING SAME AND METHODS OF PREPARATION AND USE

[75] Inventors: Malika Gunasekera; Sarath P. Gunasekera; Ross E. Longley, all of Vero Beach, Fla.; Neal S. Burres, Highland Park, Ill.

[73] Assignee: Harbor Branch Oceanographics Institution, Inc., Fort Pierce, Fla.

[21] Appl. No.: 392,468

[22] Filed: Aug. 11, 1989

[51] Int. Cl.$^5$ ................ A61K 31/365; C07D 309/14
[52] U.S. Cl. .................................. 514/459; 549/292; 514/885
[58] Field of Search ................ 549/292; 514/459, 460, 514/885

[56] References Cited

PUBLICATIONS

Y. Koto et al., *J. Am. Chem. Soc.*, "Calyculin A, a Novel Antitumor Metabolite from Marine Sponge Discodermia Calyx", 108, 2780-2781 (1986).
D. Vemura et al., *J. Am. Chem. Soc.*, "Norhalichondrin A: an Antitumor Polyether Macrolide from a Marine Sponge," 107, 4796-4798 (1985).
S. Matsunaga et al., *Tetrahedron Letters*, "Bioactive Marine Metabolites," 25(45), pp. 5165-5168 (1984).
S. Matsunaga et al., *Tetrahedron Letters*, "Bioactive Marine Metabolites," 26(7), pp. 855-856, (1985).

*Primary Examiner*—Glennon H. Hollrah
*Assistant Examiner*—Mark A. Russell
*Attorney, Agent, or Firm*—Saliwanchik & Saliwanchik

[57] ABSTRACT

Novel lactone compounds having remarkable immunomodulatory and antitumor activities, pharmaceutical compositions comprising such compounds, methods for the preparation of the novel compounds and compositions and methods of their use for therapeutic purposes are described. The new lactone compounds have the structure according to the formula:

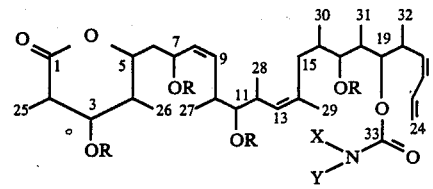

wherein:
R=—H, —A, —CH$_2$—Q, —COA or —COZ,
A=lower alkyl,
Z=monocyclicaryl,
Q=phenyl, tolyl or xylyl,
X=—H, —A, —Z or —CH$_2$—Z, and
Y=—H, —A, —Z, —CH$_2$—Z, —COA, —COZ,
the acid-addition salts, the octahydro and 23,24-dihydro derivatives thereof.

15 Claims, No Drawings

DISCODERMOLIDE COMPOUNDS, COMPOSITIONS CONTAINING SAME AND METHODS OF PREPARATION AND USE

FIELD OF THE INVENTION

This invention relates to new organic compounds and compositions which have useful therapeutic properties. More particularly, the invention concerns novel lactone compounds having immunomodulatory and antitumor activities, pharmaceutical compositions comprising such compounds, methods for the preparation of the novel compounds and compositions and methods of their use for therapeutic purposes.

BACKGROUND OF THE INVENTION

Immunomodulation is a developing segment of immunopharmacology. Immunomodulator compounds and compositions, as the name implies, are useful for modulating or regulating immunological functions in warm blooded animals. Immunomodulators may be immunostimulants for building up immunities to or initiate healing of certain diseases and disorders. Conversely, they may be immunoinhibitors or immunosuppressors for preventing undesirable immuno reactions of the body to foreign materials and autoimmue diseases.

Immunomodulators have been found to be useful for treating systemic autoimmue diseases, such as lupus erythematosus, as well as immunodeficiency diseases. Further, immunomodulators may be useful for immunotherapy of cancer or to prevent rejections of foreign organs or other tissues in transplants, e.g., kidney, heart or bone marrow.

Various immunomodulator compounds have been discovered including muramylic acid dipeptide derivatives, levamisole, niridazole, oxysuran, flagyl and others from the groups of interferons, interleukins, leukotrienes, corticosteroids and cyclosporins. Many of these compounds have been found, however, to have undesirable side effects and/or high toxicity. New immunomodulator compounds are therefore needed to provide a wider range of immunomodulator function for specific areas with a minimum of undesirable side effects.

In addition to work on immunomodulators, considerable research and resources have been devoted to oncology and antitumor measures including chemotherapy. While certain methods and chemical compositions have been developed which aid in inhibiting, remitting or controlling the growth of tumors, new methods and antitumor chemical compositions are needed.

In searching for new biologically active compounds, it has been found that some natural products and organisms are potential sources for chemical molecules having useful biological activity of great diversity. Marine sponges have proved to be such a source and a number of publications have been issued disclosing organic compounds derived from marine sponges including Scheuer, P. J. Ed., *Marine Natural Products, Chemical and Biological Perspectives;* Academic Press, New York, 1978, Vol. I, pp 175–240; Uemura et al., J. Am. Chem. Soc., 1985, 107, 4796–4798; Minale, L., et al., Fortschr. Chem. org. Naturst. 1976, 33, 1–72; Faulkner, D. J., *Nat. Prod. Rep.* 1987, 4, 539–576 and references cited therein.

The present invention has added to the arsenal of mmunomodulator and antitumor compounds by the discovery of new organic compounds possessing useful immunomodulator and antitumor activity isolated from extracts of the marine sponge *Discodermia dissoluta*.

OBJECTS

A principal object of this invention is the provision of novel biologically active, lactone compounds and compositions comprising such compounds.

Additional objects are the provision of methods for producing the new compounds and compositions.

Yet another object is the provision of methods of using the new compounds and compositions, particularly, methods to modify immune systems, inhibit tumor growth and mitigate cancerous cachexia.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

SUMMARY OF THE INVENTION

The objects of the invention are accomplished by the provision of novel, biologically active compounds that have a structure according to the formula:

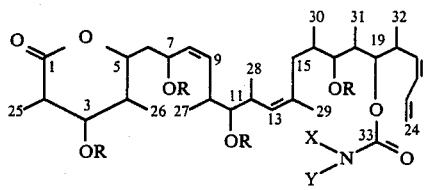

wherein:
R = —H, —A, —CH$_2$—Q, —COA or —COZ,
A = lower alkyl,
Z = monocyclicaryl,
Q = phenyl, tolyl or xylyl,
X = —H, —A, —Z or —CH$_2$—Z, and
Y = —H, —A, —Z, —CH$_2$—Z, —COA, —COZ, and acid-addition salts thereof.

Compounds of the invention also include the octahydro and 23,24-dihydro derivatives of compounds according to the above formula. The new compounds may be a single geometrical isomer or mixtures thereof (E or Z isomer).

Preferred compounds of the invention are represented by the formula:

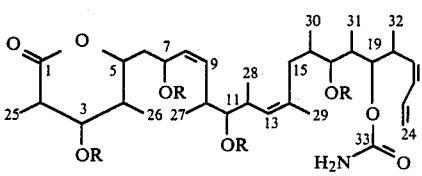

wherein R = —H, or —COCH$_3$, or —CH$_3$. and by the formula:

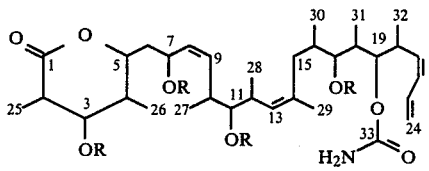

In preferred embodiments of the invention, the new compounds are substantially pure, i.e., contain at least 95% of the compound as determined by established analytical methods.

Specific examples of lower alkyl groups A in compounds of the invention preferably contain 1–6 carbon atoms and include methyl, ethyl, propyl, isopropyl, butyl, isobutyl, amyl, 2,2-dimethylpropyl, hexyl and 2-ethylamyl.

Specific examples of monocyclicaryl groups Z in compounds of the invention include phenyl, p-tolyl, m-tolyl, p-bromophenyl, p-chlorophenyl, 3-ethyl-4-bromophenyl, 2,4-diethylphenyl, 2-methyl-3-hydroxyphenyl, 2,4-dimethyl-3-chlorophenyl, 2-bromo-3-amino-4-methylphenyl and 2-iodo-3-ethyl-5-aminophenyl.

Also provided by the discoveries of the invention are new pharmaceutical compositions containing between about 0.1% to 55% by weight, particularly 1% to 30%, based on the total weight of the composition, of one of the new compounds of the invention or a mixture of two or more such compounds and one or more pharmaceutically acceptable carrier or diluent.

The invention provides a variety of processes for the production of compounds of the invention. A preferred method of producing them comprises the steps of collecting marine sponge of the species *Discodermia dissoluta*, extracting such sponge with a selected organic solvent system to obtain an extract, fractioning the extract and isolating lactone compounds from the fractioned extract.

The sponge Discodermia has two literature references.

1. Y. Kato, N. Fusetani, S. Matsunaga and K. Hashimoto. *J. Amer. Chem. Soc.*, 108, 2780, 1986.

2. S. Matsunasa, N. Fusetani and S. Konosa, Tetrahedron Letters, 25, 5165, 1985: 26, 855, 1985.

In further preferred methods of the invention, new salts within the scope of the invention are made by adding mineral acids, e.g., HCl, $H_2SO_4$, etc., or strong organic acids, e.g., formic, oxalic, etc., in appropriate amounts to form the acid addition salt of the parent compound its derivative. Also synthesis type reactions may be used pursuant to known procedures to add or modify various groups in the preferred compounds to produce other compounds within the scope of the invention.

As a result of the discoveries by the invention of the new compounds and their structuring, skilled chemists will be able to use known procedures to synthesize them from available stock substances.

As embodied and fully described herein, the invention also comprises methods of use of the new compounds and compositions of the invention, e.g., methods of inhibiting tumors in a mammal, therapeutic methods for treating cancerous cachexia and methods of regulating immunological functions in warm blooded animals.

In accordance with the invention, methods for inhibiting tumors in a host comprise contacting tumor cells with an effective amount of the new pharmaceutical compositions of the invention.

DESCRIPTION OF THE PREFERRED EMBODIMENTS

A more complete understanding of the invention can be obtained by reference to preferred embodiments of the invention which are illustrated by the following specific examples of compounds, compositions and methods of the invention. It will be apparent to those skilled in the art that the examples involve use of materials and reagents that are commercially available from known sources, e.g., chemical supply houses, so no details are given respecting them.

EXAMPLE 1

This example concerns the preparation of discodermolide having the formula:

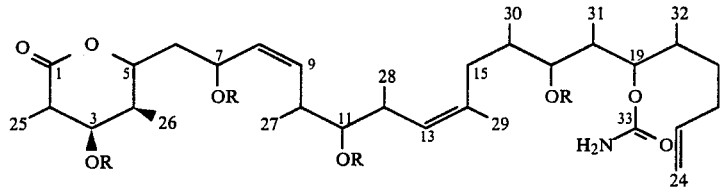

The sponge *Discodermia dissoluta* was homogenized with methanol-toluene (3:1). After filtration and evaporation at reduced pressure below 35° C., a brown colored extract was obtained. The extract was then partitioned between EtOAc and $H_2O$. The biologically active EtOAc soluble fraction was fractionated first by column chromatography on $SiO_2$ gel using $CH_2Cl_2$ and MeOH gradient and monitored by biological activity. The biologically active (AT, ID) fraction was chromatographed on RP-C18 with $H_2O$-MeOH gradient. The fractions that eluted with (30–70% $H_2O$-MeOH) gave impure discodermolide.

The impure compound was then subjected to HPLC (RP C-18, 5μ, 250×10 mm) using 48% $H_2O$-MeOH as eluent to give pure discodermolide (I), white crystals; m.p. 115°–116°, $(\alpha)^{25}$ D=7.2° (c=0.72); UV λ max (MeOH) 235 nm ($\epsilon$=12500), 226sh (19500), 210 (35400); Ir (CHCl$_3$) 3610, 3500, 3415, 3158, 2976, 2928, 1725, 1580, 1460, 1375, 1100, 1037 cm$^{-1}$;

$^1$H NMR (CDCl$_3$ & 5% CD$_3$OD) δ 6.54 (1H, ddd J=16.6, 11.3, 10.0 Hz, H23), 5.95 (1H, ddd, J=11.3, 10.5, 1.1 Hz, H22), 5.37 (1H, dd, J=10.0, 7.6 Hz, H8), 5.34 (1H, dd, J=10, 9.4 Hz, H9), 5.28 (1H, dd, J=10.5, 10.5 Hz, H21), 5.13 (1H, d, J=16.6 Hz, H24), 5.05 (1H, d J=10 Hz, H24), 5.09 (1H, d, J=9.9 Hz, H13), 4.60 (1H, m, H7), 4.63 (1H, dd, J=6.1, 6.1 Hz, H19), 4.50 (1H, dt, J=9.7, 2.3 Hz, H5), 3.57 (1H, t, J=4.0 Hz, H3), 3.15 (1H, t, J=5.5 Hz, H17), 3.09 (1H,t, J=6.3 Hz, H11), 2.95 (1H, ddq, J=10.5, 6.1, 6.6 Hz, H20), 2.65 (1H, ddq, J=9.4, 6.3, 6.6 Hz, H10), 2.58 (1H, dq, J=4.0, 7.3 Hz, H2), 2.45 (1H, ddq, J=9.9, 6.3, 6.6 Hz, H12), 1.82 (1H, ddq, J=4.0, 2.3, 7.1 Hz, H4), 1.84, 1.70 (2H,m, H15), 1.80 (1H, ddq, J=6.1, 5.5, 6.8 Hz, H18), 1.80 (1H, m, H16), 1.74 (1H, m, H6), 1.59 (1H, m, H6), 1.54 (3H, s, H29), 1.28 (3H, d, J=7.3 Hz,H25), 0.97 (3H, d, J=7.1 Hz, H26), 0.94 (3H, d, J=6.6 Hz, H27). 0.92 (3H, d, J=6.6 Hz, H32), 0.87 (3H, d, J=6.8 Hz, H31), 0.85 (3H, d, J=6.6 Hz, H28), 0.74 (3H, d, J=6.5 Hz, H30);

$^{13}$C NMR (CDCl$_3$ & 5% CD$_3$OD) δ 175.2 (s, Cl), 157.7 (s,C33), 134.27 (d, C9), 133.3 (d, C21), 132.7 (s, C14), 131.9 (d, C23), 129.7 (d, C22), 132.4 (d, C8), 129.9 (d, C13), 117.8 (t, C24), 75.6 (d,C17) 78.8 (d, C19), 78.9 (d, C11), 77.0 (d, C5), 72.5 (d, C3), 63.4 (d,C7), 42.9 (d, C2) 40.9 (t, C6), 37.1 (d, C18), 35.6 (t, C15), 36.0 (d, C10), 34.4 (d, C20), 35.1 (d, C12), 35.4 (d, C4), 33.0 (d, C16), 22.9 (q, C29), 17.3 (q, C32), 18.0 (q, C27), 15.6 (q, C28), 15.5 (q, C25), 13.7 (q, C30), 12.4 (q, C26), 8.6 (q, C31).

EXAMPLE 2

This example concerns the preparation of discodermolide tetra-acetate having the formula:

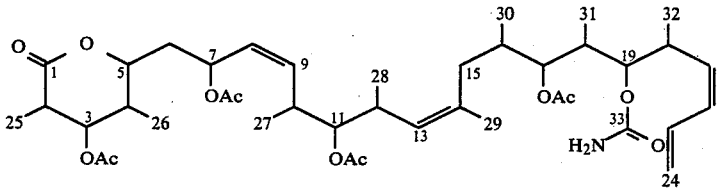

Acetylation of discodermolide with acetic anhydride and pyridine at room temperature furnished discodermolide tetra-acetate, a colorless gum; (α)$^{25}$ D=19.2° (c=0.3, CHCl$_3$); UV λ max (EtOH) 235 nm (ε=12,000), 227sh (21000), 222 (21400), 205 (41000);

IR (CHCl$_3$) 3537, 3423, 2962, 1735, 1727, 1585, 1510, 1370, 1327, 1222, 1100, 1023, 965, 912, cm$^{-1}$.

$^1$NMR (CDCl$_3$) δ 6.71 (1H, dddd, J=16.6, 11.3, 10.0, 1.3 Hz, H23), 6.03 (1H, ddd, J=10.5, 11.3, 1.1 Hz, H22), 5.65 (1H, ddd, J=1.8, 8.3, 10.0 Hz, H7), 5.49 (1H, dd, J=10.7, 10.7 Hz, H9), 5.31 (1H, ddd, J=10.5, 10.5, 1.3Hz, H21), 5.28 (1H, ddd, J=10.7, 10.0, 1.0 Hz, H8), 5.21 (1H, d, J=10.0 Hz, H24), 5.15 (1H, dd, J=16.6, 1.1 Hz, H24), 4.94 (1H, d, J=9.9 Hz, H13), 4.89 (1H, dd, J=5.8, 5.8 Hz, H3), 4.78 (1H, dd, J=5.8, 5.6 Hz, H17 , 4.60(1H, dd, J=6.1, 6.1 Hz, H19), 4.60 (2H, br s, NH$_2$), 4.27 (1H, dd, J=4.8, 6.4 Hz, H11), 4.26 (1H, dt, J=2.0, 9.7 Hz, H5), 3.12 (1H, ddq, J=6.1, 10.5, 6.6 Hz, H20), 2.89 (1H, ddq, J=10.7, 6.4, 6.6 Hz, H10), 2.70 (1H, dq J=5.8, 7.3 Hz, H2), 2.47 (1H, ddq, J=9.9, 4.8, 6.6 Hz, H12), 2.10 (1H, ddd, J=12.6, 9.7,8.3 Hz, H6), 2.09 (1H, ddq, J=5.8, 2.0, 6.9 Hz, H4), 2.08 (3H, s, H35), 2.08(3H, s, H41), 2.03 (1H, dddq, J=11.8, 10.0, 5.8, 6.6 Hz, H16), 2.02 (3H, s, H37), 2.00 (3H, s, H39), 1.98 (1H, ddq, J=6.1, 5.6, 6.8 Hz, H18), 1.86 (1H,dd, J=12.6, 11.8 Hz, H15), 1.67 (1H, dd, J=12.6, 10.0 Hz, H15), 1.64 (1H, ddd, J=12.6, 9.7, 1.8 Hz, H6), 1.61 (3H, s, H29), 1.29 (3H, d, J=7.3, Hz,H25), 0.97 (3H, d, J=6.9 Hz, H26), 0.96 (3H, d, J=6.6 Hz, H32), 0.95 (3H, d,J=6.6 Hz, H27), 0.89 (3H, d, J=6.8 Hz, H31), 0.85 (1H, d, J=6.6 Hz, H28), 0.68 (3H, d, J=6.6 Hz, H30);

$^{13}$C NMR (CDCl$_3$) δ 171.7 (s, Cl), 170.9 (s,C34), 170.6 (s, C36), 170.4 (s, C40), 169.8 (s, C38), 156.7 (s, C33), 135.1 (d, J=160 Hz, C9), 133.4 (s, C14), 133.0 (d, J=159 Hz, C21), 132.2 (d, J=153 Hz, C23), 130.2 (d, J=159 Hz, C22), 128.9 (d, J=147 Hz, C13), 128.2 (d, J=161 Hz, C8), 118.2 (t, J=160 Hz, C24), 80.2 (d, J=151 Hz,C11), 77.9 d, J=145 Hz, C17), 77.8 (d, J=145 Hz, C19), 76.8 (d, J=147Hz, C5), 74.5 (d, J=156 Hz, C3), 66.5 (d, J=148 Hz, C7), 40.0 (d, J=130Hz, C2), 38.7 (t, J 126 Hz, C6), 36.4 (d, J=123 Hz, C18), 35.6 (t, J=125Hz, C15), 35.1 d, J=124 Hz, C10), 34.1 (d, J=126 Hz, C20), 34.1 (d, J=126 Hz, C12), 33.7 (d, J=127 Hz, C4), 31.8 (d, J=124 Hz, C16), 22.8 (q, J=123 Hz, C29), 21.2 (q, J=127 Hz, C41), 20.9 (q, J=127 Hz, C37), 20.9 (q, J=127 Hz, C39), 20.9 (q, J=127 Hz, C35), 17.5 (q, J=124 Hz, C32), 17.5 (q, J=124 Hz, C27), 16.6 (q, J=124 Hz, C28), 15.3 (q, J=124 Hz, C25), 13.6 (q, J=124 Hz, C30), 12.4 (q, J=124 Hz, C26), 9.5 (q, J=121 Hz, C31);

HRFAB: m/z 702.4203 Δ1.4 mmμ for C$_{39}$H$_{60}$NO$_{10}$ (MCH$_3$COO)$^+$; LRFAB: m/z (relative intensity) 762(3%), 702(5), 642(2), 581(4), 521(7), 439(3), 427(5), 411(4), 399(5), 387(12), 359(9), 334(11), 327(5), 299(5), 285(5), 259(6), 232(20), 217(75), 173(42), 161(72), 147(50), 133(80), 126(100).

EXAMPLE 3

This example concerns the preparation of the octahydro derivative of discodermolide which is represented by the formula:

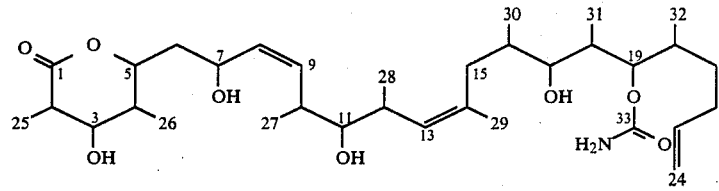

A portion of discodermolide and a small amount of hydrogenation catalyst, e.g., Pd/C, Pt oxide or Raney are mixed in a suitable solvent, e.g., ethanol or methanol. The mixture is stirred in the presence of hydrogen in a hydrogenation apparatus capable of operation at elevated pressure, e.g., Parr apparatus, to produce octahydro discodermolide. If the reaction is too slow, it is facilitated by making the media slightly acidic. Partial reduction of discodermolide to the 23,24-dihydro derivative can be attained by hydrogenation at ambient pressure conditions.

EXAMPLE 4

This example concerns the preparation of the methyl ether of discodermolide represented by the formula:

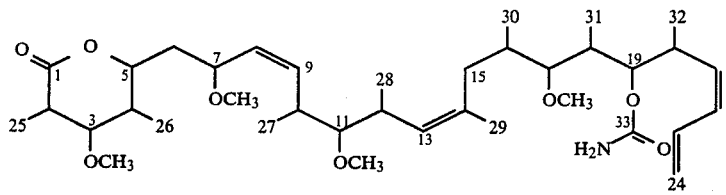

A portion of discodermolide was mixed with methyl iodide in dry acetone containing anhydrous $K_2CO_3$ and refluxed for 12 hrs. The mixture was filtered and the solvent evaporated under vacuum. The residue was chromatographed on silica gel to give a product, the tetramethyl ether.

BIOLOGICAL ACTIVITY EVALUATION

Immunomodulator Methodology

The crude ethanolic extract was tested in the two-way mixed lymphocyte reaction (MLR) and a lymphocyte viability assay (LCV) at 500 and 50 µg/ml, using murine splenocytes. Cellular proliferation was measured using a modified form of the M.T.T. assay (Mosmann, T. 1983. Rapid colorimetric assay for cellular growth and survival: (Application to proliferation and cytotoxicity assays. *J. Immunol. Methods* 65:55–63). Responses were reported as a percent of the positive MLR or LCV control.

The pure compound discodermolide I, was tested for immunosuppressive effects on the MLR and LCV assays using murine splenocytes and in the human MLR and mitogen stimulation assays, using human peripheral blood lymphocytes (PBL). Cellular proliferation was determined using incorporation of $^3H$-thymidine.

Antitumor Methodology

The crude ethanolic extract of the sponge and the pure compound I were tested for toxicity against murine P388 leukemia cells. P388 cells obtained from Dr. J. Mayo, National Cancer Institute, Bethesda, MD, were maintained in Roswell Park Memorial Institute (RPMI) medium 1640 supplemented with 10% horse serum. All cell lines were cultured in plastic tissue culture flasks and kept in an incubator at 37° C. in humidified air containing 5% $CO_2$. Antibiotic-free stock cultures of P388 cells were subcultured to $10^5$ cells/ml by dilution in fresh growth medium at 2 to 3 day intervals. The mean generation time of primary cultures was 14 to 17 hr.

To assess the antiproliferative effects of agents against P388 cells, 200 µl cultures (96-well tissue culture plates, Nunc, Denmark) were established at $1 \times 10^5$ cells/ml in drug-free medium or medium containing the crude extract at a final dilution of 1:500 or discodermolide at various concentrations. Solvent for all dilutions was methanol, which was removed from plates under vacuum. All experimental cultures were initiated in medium containing Gentamycin sulfate (50 µg/ml; Schering Corporation, Kenilworth, NJ). After 48-h exposures, P388 cells were enumerated using 3-[4,5-Dimethylthiazol-2-yl]-2,5-diphenyltetrazolium bromide (MTT) as described below (M. C. Alley, et al., *Cancer Res.* 48:589, 1988).

To quantitate the effects on cell proliferation, 75 µl of warm growth medium containing 5 mg/ml MTT was added to each well and cultures were returned to the incubator for 90 minutes. To spectrophotometrically quantitate formation of reduced formazan, plates were centrifuged (900×g, 5 minutes), culture fluids removed by aspiration, and 200 µl of acidified isopropanol (2 ml concentrated HCl/liter isopropanol) added per well. The absorbance of the resulting solutions were measured at 570 nm with a plate reader (MR700 Microplate Reader, Dynatech, Laboratories, Chantilly, Va.). The absorbance of test wells was divided by the absorbance of drug-free wells, and the concentration of agent that resulted in 50% of the absorbance of untreated cultures was determined by linear regression of logit-transformed data (D. J. Finney, Statistical Method in Biological Assay, third ed., pp. 316–348, Charles Griffin Co., London, 1978). A linear relationship between P388 cell number and formazan production was found over the range of cell densities observed in these experiments.

Immunomodulator Activity

The crude extract was immunosuppressive in the MLR at a 1× concentration (<1% of the control MLR response, but exhibited toxicity (<6% of the control LCV response) at the same dosage level. Immunosuppressive activity was observed at a 1/10 dilution of the crude extract (<1% of the control MLR) which was associated with relatively low toxicity (<70% of the control LCV response).

Discodermolide was immunosuppressive in the murine MLR with no associated toxicity at a dosage of 0.5 µg/ml. Higher dilutions (500, 50 and 5 µg/ml) exhibited immunosuppressive activity, but with associated toxicity (Table 1). In the human MLR, Discodermolide was immunosuppressive with >94% viability at 50, 25, 12.5, 6.3, 3.1 and 1.6 µg/ml (FIG. 2). Discodermolide suppressed Con A and PHA (10 µg/ml) stimulation of human PBL at 50 and 25 µg/ml, with >91% viability (Table 3).

TABLE 1

Immunosuppressive Effect of Discodermolide On The Murine Mixed Lymphocyte Reaction

| Conc. | µg/ml | [1]% MLR Control | [2]% LCV Control |
|---|---|---|---|
| 0.0 | (control) | 100 | 90 |
| 0.5 | | 18 | 151 |
| 5 | | 25 | 68 |
| 50 | | <1 | 26 |
| 500 | | <1 | <1 |

[1]Percent of the control MLR response.
[2]Percent of the control LCV response.

TABLE 2

Immunosuppressive Effect of Discodermolide On The Human Mixed Lymphocyte Reaction

| Conc. | µg/ml | [1]CPM | [2]% Viability |
|---|---|---|---|
| 0.0 | (control) | 48064 | 100 |

TABLE 2-continued

Immunosuppressive Effect of Discodermolide On
The Human Mixed Lymphocyte Reaction

| Conc. μg/ml | [1]CPM | [2]% Viability |
|---|---|---|
| 0.4 | 64211 | 115 |
| 0.8 | 49509 | ND |
| 1.6 | 26336 | 110 |
| 3.1 | 8532 | 94 |
| 6.3 | 4996 | 94 |
| 12.5 | 2091 | 94 |
| 25 | 1728 | 102 |
| 50 | 1932 | 204 |

[1]Counts per minute of incorporate $^3$H-thymidine
[2]% Viable cells as measured by M.T.T. metabolism

TABLE 3

Immunosuppressive Effect of Discodermolide On
Con A and PHA Mitogenesis of Human Lymphocytes

| Conc. μg/ml | [1]Con A | [2]PHA |
|---|---|---|
| 0.0 (control) | 262000 | 412200 |
| 6.3 | 299518 | 441580 |
| 12.5 | 213740 | 391633 |
| 25 | 11567 | 14425 |
| 50 | 10230 | 16984 |

[1]Counts per minute of incorporated $^3$H-thymidine. Conc. of Con A = 10.0 μg/ml
[2]Counts per minute of incorporated $^3$H-thymidine. Conc. of PHA = 10.0 μg/ml

Antitumor Activity

A 1:500 dilution of the crude extract inhibited the proliferation of cultured murine P388 leukemia cells by 91%.

Discodermolide inhibited the proliferation of cultured murine P388 cells. The concentration resulting in 50% inhibition (IC50) was 0.5 μg/ml as reported in the following Table 4.

TABLE 4

P388 Cytotoxicity

| Concentration (μg/ml) | % Inhibition |
|---|---|
| 20 | 92 |
| 10 | 90 |
| 5 | 88 |
| 2.5 | 87 |
| 1.0 | 75 |
| 0.5 | 49 |
| 0.25 | 12 |
| 0.125 | 2 |

Discussion of Variables

The scope of the invention is not limited by the specific examples and suggested procedures and uses related herein since modifications can be made within such scope from the general information provided by this specification to those skilled in the art.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include, ethanol, dimethyl sulfoxide, glycerol, silica, alumina, starch, and equivalent carriers and diluents.

The new compounds are useful as immunomodulatory agents. An intended use is for immune reactions (in vivo/in vitro) that require modulation via T-cell activity. Direct application would be for human in vivo suppression of T-cell responses, e.g., transplantation and autoimmunity.

In preferred embodiments for production of the new compounds by extraction from marine sponges, etc., suitable organic solvent systems for extraction can be selected from methanol, ethyl acetate, toluene, heptane, hexane, isooctane, acetone, benzene, diethyl ether, t-butyl methyl ether, ethanol, isopropanol, 1,2 dichloroethane and especially, chloroform, ammonium hydroxide and dichloromethane. Mixtures of two or more of such solvents in various ratios and combinations are advantageous.

Compounds of the invention are isolated by various fractionation and chromatographic techniques from the extracts obtained as disclosed. Preferred isolation procedures include various chromatography techniques, e.g., countercurrent chromatography with suitable columns, including multi-layer planetary coil columns. A variety of solvents are available for use as single or mixed eluents, such as methylene chloride, methanol, ethyl acetate, acetonitrile, n-propanol, n-butanol, water, dilute sulfuric acid, and equivalent solvents. Further purifications using such procedures may also be carried out on the recovered extractions. Preferred isolation techniques for further purification include chromatographic operations such as high-pressure, liquid chromatography with suitable columns with suitable solvent, particularly, methylene chloride/methanol or methanol/water mixtures.

The embodiments of the invention in which an exclusive property or privilege is claimed are defined as follows:

1. A compound of the formula:

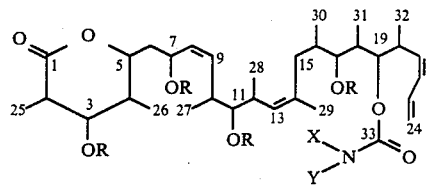

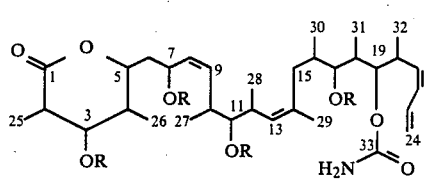

wherein:
R=—H, —A, —CH$^2$—Q, —COA or —COZ,
A=lower alkyl,
Z=
phenyl, p-tolyl, m-tolyl, p-bromophenyl, p-chlorophenyl, 3-ethyl-4-bromophenyl, 2,4-diethylphenyl, 2-methyl-3-hydroxyphenyl, 2,4-dimethyl-3-chlorophenyl, 2-bromo-3-amino-4-methylphenyl, and 2-iodo-3-ethyl-5-aminophenyl
Q=phenyl, tolyl or xylyl, X=—H, —A, —Z or —CH$_2$—Z, and Y=—H, —A, —Z, —CH$_2$—Z, —COA, —COZ, and acid-addition salts thereof.

2. A compound of the formula:

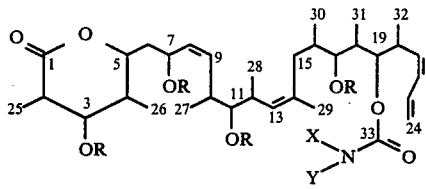

wherein R=—H, —COCH$_3$ or —CH$_3$ and acid-addition salts thereof.

3. A compound of claim 2 wherein R is —H.

4. A compound of claim 2 wherein R is —COCH$_3$.

5. A compound of claim 2 wherein R is —CH$_3$.

6. The octahydro derivative of a compound of claim 1.

7. A compound of claim 6 wherein R=—H, —COCH$_3$ or —CH$_3$, X=—H and Y=—H.

8. The 23,24 dihydro derivative of a compound of claim 1.

9. The octahydro derivative of a compound of claim 2.

10. The 23,24 dihydro derivative of a compound of claim 2.

11. A pharmaceutical composition comprising between about 0.1 to 55% by weight based on the total weight of said composition as an active ingredient one compound or mixture of two or more compounds of the formula:

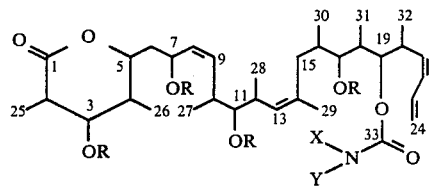

wherein:
R=—H, —A, —CH$_2$—Q, —COA or —COZ,
A=lower alkyl,
Z=
phenyl, p-tolyl, m-tolyl, p-bromophenyl, p-chlorophenyl, 3-ethyl-4-bromophenyl, 2,4-diethylphenyl, 2-methyl-3-hydroxyphenyl, 2,4-dimethyl-3-chlorophenyl, 2-bromo-3-amino-4-methylphenyl, 2-iodo-3-ethyl-5-aminophenyl,
Q=phenyl, tolyl or xylyl,
X=—H, —A, —Z or —CH$_2$—Z, and
Y=—H, —A, —Z, —CH$_2$—Z, —COA, —COZ, and acid-addition salts thereof and
a non-toxic pharmaceutically acceptable carrier or diluent.

12. A pharmaceutical composition comprising a between about 0.1 to 55% by weight based on the total weight of said composition as an active ingredient a compound of claim 2 and a non-toxic pharmaceutically acceptable carrier or diluent.

13. A method of modulating and/or regulating immunological functions in humans and warm-blooded animals which comprises administering to said human or animal an effective immunomodulatory amount of one or more compounds of claim 1.

14. A method of modulating and/or regulating immunological functions in humans and warm-blooded animals which comprises administering to said human or animal an effective immunomodulatory amount of one or more compounds of claim 2.

15. A method of modulating and/or regulating immunological functions in humans and warm-blooded animals which comprises administering to said human or animal an effective immunomodulatory amount of one or more compounds of claim 6.

* * * * *

UNITED STATES PATENT AND TRADEMARK OFFICE
CERTIFICATE OF CORRECTION

Page 1 of 9

PATENT NO. : 4,939,168

DATED : August 11, 1990

INVENTOR(S) : Malika Gunaskera, Sarath Gunasekera, Ross E. Longley, Neal S. Burres It is certified that error appears in the above-identified patent and that said Letters Patent is hereby corrected as shown below:

Column 1: line 26: "Autoimmue" should read --Autoimmune--; line 29: "Autoimmue" should read --Autoimmune--; line 68: "mmunomodulator" should read --immunomodulator--.

Column 3: line 1:

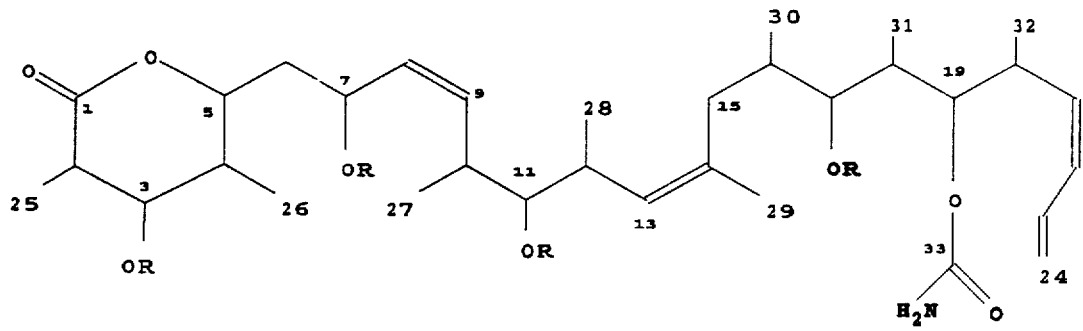

UNITED STATES PATENT AND TRADEMARK OFFICE
CERTIFICATE OF CORRECTION

PATENT NO. : 4,939,168

DATED : August 11, 1990

INVENTOR(S) : Malika Gunaskera, Sarath Gunasekera, Ross E. Longley, Neal S. Burres It is certified that error appears in the above-identified patent and that said Letters Patent is hereby corrected as shown below:

Should read

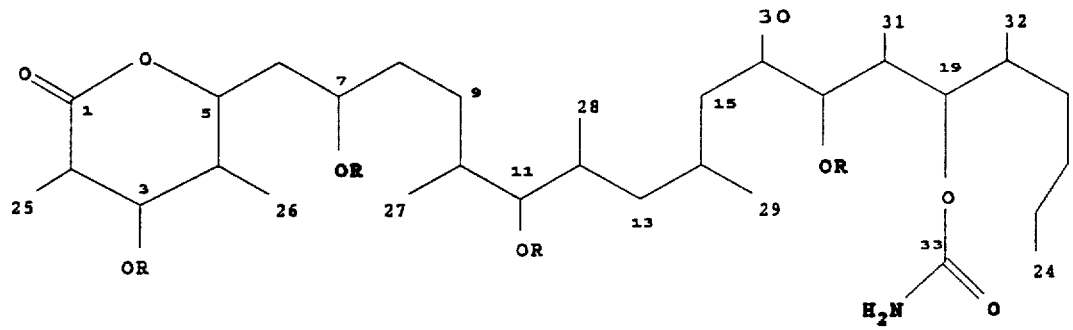

Column 4: line 62: "Also" should read --Also,--.
line 29:

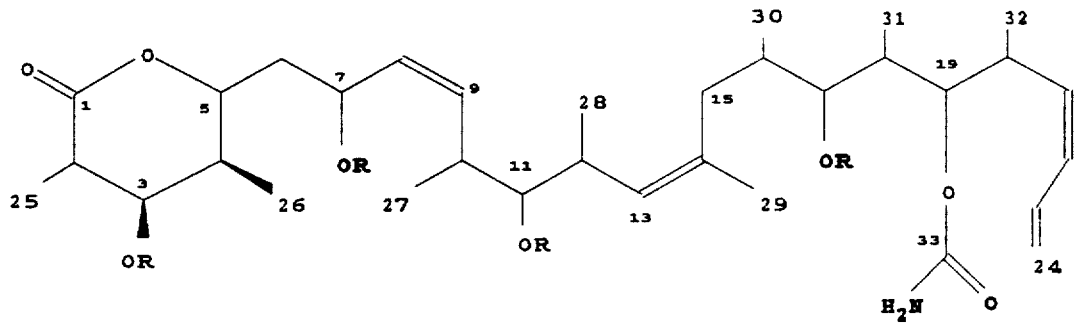

UNITED STATES PATENT AND TRADEMARK OFFICE
CERTIFICATE OF CORRECTION

PATENT NO. : 4,939,168

DATED : August 11, 1990

INVENTOR(S) : Malika Gunaskera, Sarath Gunasekera, Ross E. Longley, Neal S. Burres It is certified that error appears in the above-identified patent and that said Letters Patent is hereby corrected as shown below:

Should read

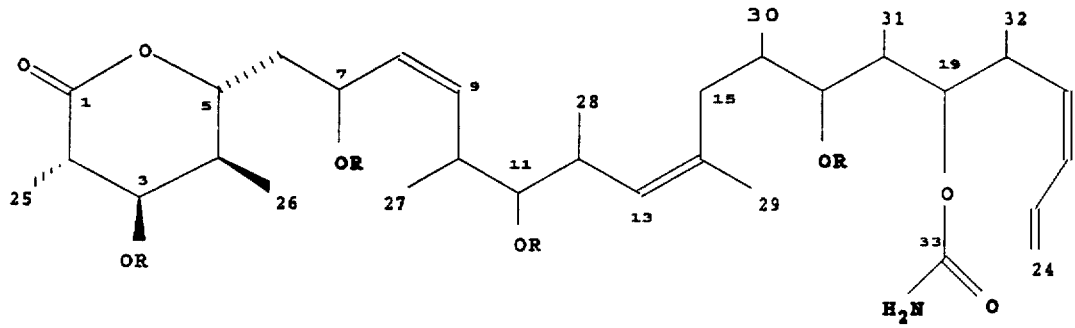

Column 5:   line 56: "H17," should read --H17)--.

UNITED STATES PATENT AND TRADEMARK OFFICE
CERTIFICATE OF CORRECTION

Page 4 of 9

PATENT NO. : 4,939,168

DATED : August 11, 1990

INVENTOR(S) : Malika Gunaskera, Sarath Gunasekera, Ross E. Longley, Neal S. Burres It is certified that error appears in the above-identified patent and that said Letters Patent is hereby corrected as shown below:

Column 6: line 45:

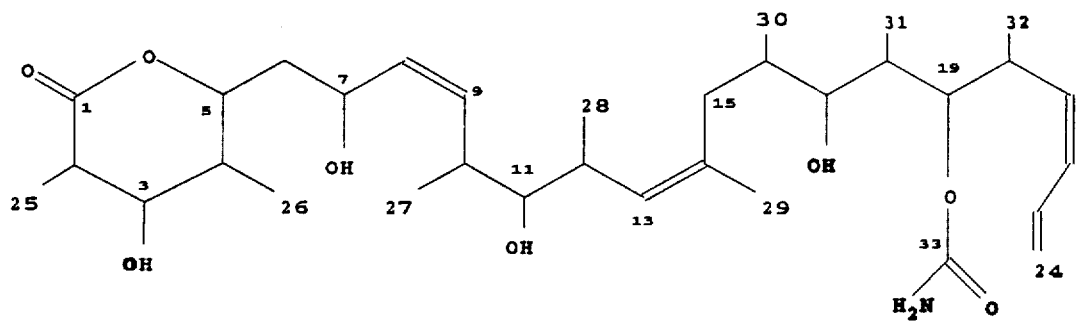

Should read

UNITED STATES PATENT AND TRADEMARK OFFICE
CERTIFICATE OF CORRECTION

PATENT NO. : 4,939,168

DATED : August 11, 1990

INVENTOR(S) : Malika Gunaskera, Sarath Gunasekera, Ross E. Longley, Neal S. Burres It is certified that error appears in the above-identified patent and that said Letters Patent is hereby corrected as shown below:

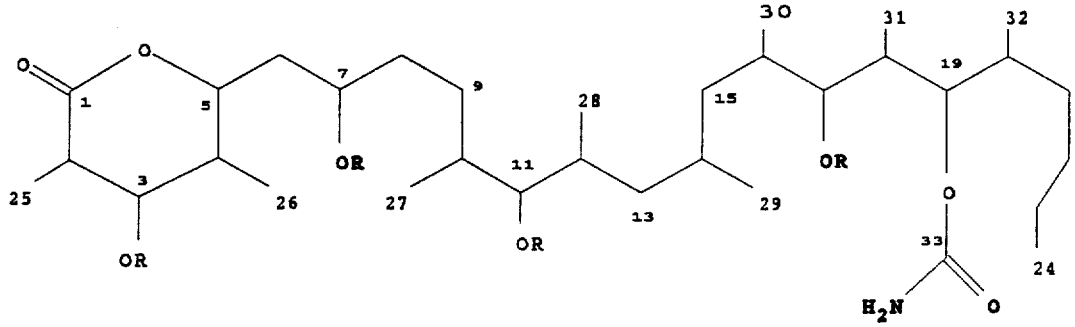

Column 8:  line 59: "Raney" should read --Raney Ni--.
           line 49: "50and" should read --50 and--.

UNITED STATES PATENT AND TRADEMARK OFFICE
CERTIFICATE OF CORRECTION

PATENT NO. : 4,939,168

DATED : August 11, 1990

INVENTOR(S) : Malika Gunaskera, Sarath Gunasekera, Ross E. Longley, Neal S. Burres It is certified that error appears in the above-identified patent and that said Letters Patent is hereby corrected as shown below:

Column 10:   claim 1

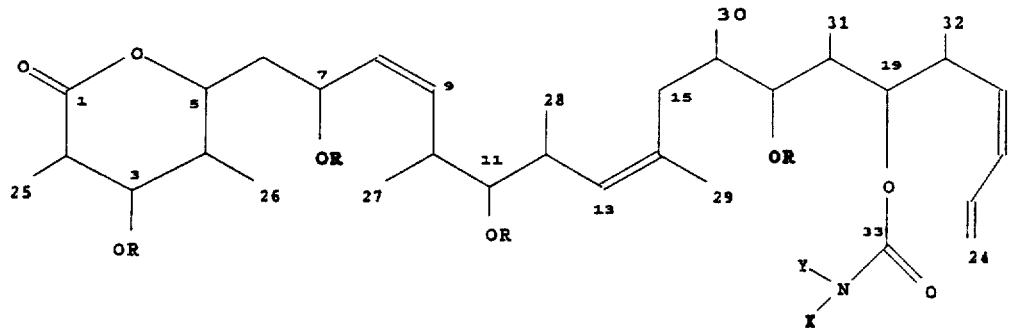

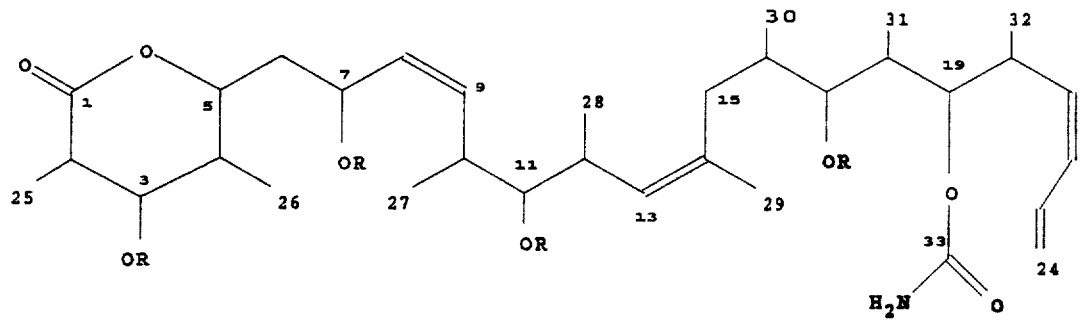

UNITED STATES PATENT AND TRADEMARK OFFICE
CERTIFICATE OF CORRECTION

PATENT NO. : 4,939,168

DATED : August 11, 1990

INVENTOR(S) : Malika Gunaskera, Sarath Gunasekera, Ross E. Longley, Neal S. Burres It is certified that error appears in the above-identified patent and that said Letters Patent is hereby corrected as shown below:

Should read

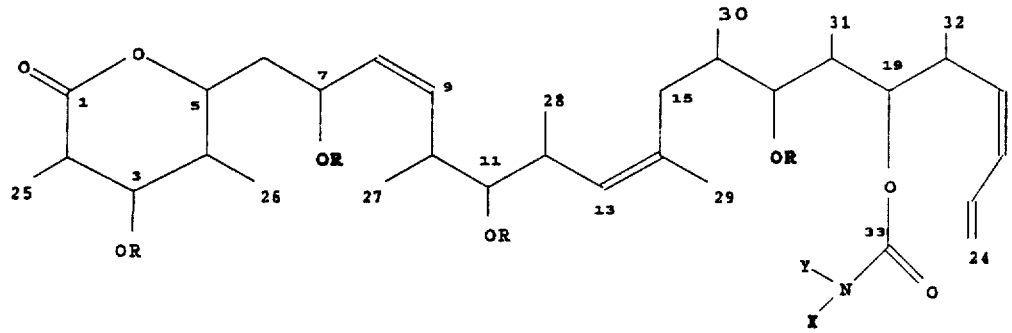

UNITED STATES PATENT AND TRADEMARK OFFICE
CERTIFICATE OF CORRECTION

Page 8 of 9

PATENT NO. : 4,939,168

DATED : August 11, 1990

INVENTOR(S) : Malika Gunaskera, Sarath Gunasekera, Ross E. Longley, Neal S. Burres It is certified that error appears in the above-identified patent and that said Letters Patent is hereby corrected as shown below:

Column 11: claim 2

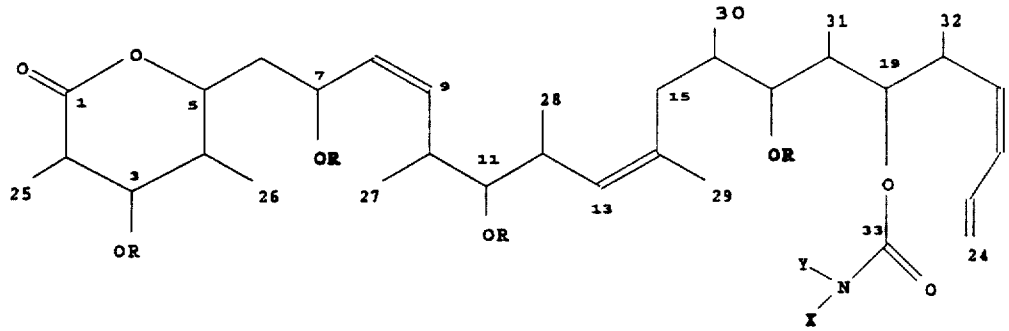

Should read

UNITED STATES PATENT AND TRADEMARK OFFICE
CERTIFICATE OF CORRECTION

Page 9 of 9

PATENT NO. : 4,939,168

DATED : August 11, 1990

INVENTOR(S) : Malika Gunaskera, Sarath Gunasekera, Ross E. Longley, Neal S. Burres It is certified that error appears in the above-identified patent and that said Letters Patent is hereby corrected as shown below:

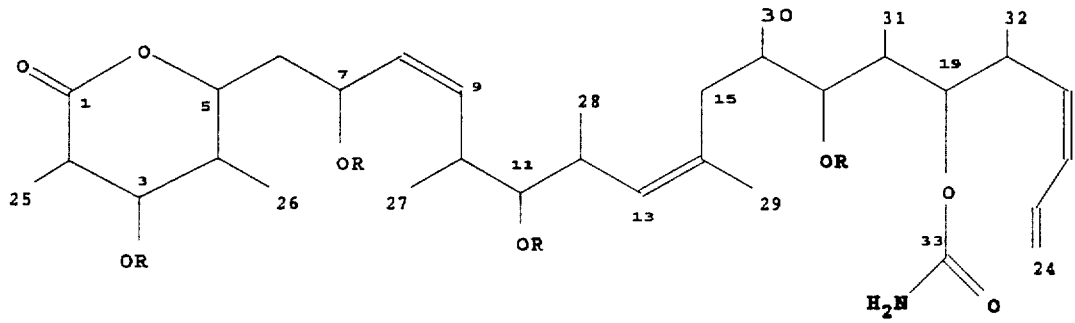

Signed and Sealed this

Tenth Day of March, 1992

Attest:

HARRY F. MANBECK, JR.

Attesting Officer      Commissioner of Patents and Trademarks